US008588499B2

(12) United States Patent
Kubo et al.

(10) Patent No.: US 8,588,499 B2
(45) Date of Patent: Nov. 19, 2013

(54) IMAGE PROCESSING METHOD, IMAGE PROCESSING SYSTEM, AND X-RAY COMPUTED TOMOGRAPHY SYSTEM

(75) Inventors: Takashi Kubo, Hitachinaka (JP); Takahito Hashimoto, Hitachinaka (JP); Toshie Yaguchi, Omitama (JP); Norio Baba, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/810,034

(22) PCT Filed: Jul. 14, 2011

(86) PCT No.: PCT/JP2011/066035
§ 371 (c)(1),
(2), (4) Date: Mar. 29, 2013

(87) PCT Pub. No.: WO2012/008512
PCT Pub. Date: Jan. 19, 2012

(65) Prior Publication Data
US 2013/0202180 A1 Aug. 8, 2013

(30) Foreign Application Priority Data

Jul. 15, 2010 (JP) .................................. 2010-160529

(51) Int. Cl.
*G06K 9/00* (2006.01)
(52) U.S. Cl.
USPC .......................................... 382/131; 382/132
(58) Field of Classification Search
None
See application file for complete search history.

(56) References Cited

U.S. PATENT DOCUMENTS

| 4,866,612 A | 9/1989 | Takagi et al. |
| 2008/0165920 A1* | 7/2008 | De Man et al. ................. 378/17 |
| 2009/0310845 A1* | 12/2009 | Ogawa et al. ................. 382/132 |

FOREIGN PATENT DOCUMENTS

| JP | 62-219076 A | 9/1987 |
| JP | 2005-326332 A | 11/2005 |

(Continued)

OTHER PUBLICATIONS

International Search Report with English translation dated Aug. 23, 2011 (four (4) sheets).

(Continued)

*Primary Examiner* — Samir Ahmed
*Assistant Examiner* — Siamak Harandi
(74) *Attorney, Agent, or Firm* — Crowell & Moring LLP

(57) ABSTRACT

Disclosed is image processing: that significantly reduces false images and missing images in reconstructed images, improves reconstruction accuracy; and that can be applied to objects to be observed that are composed of a plurality of components, and to samples having an unknown number of structural compositions. An image processing device is provided with: a means, in an electron microscope having an imaging device and a tilting device that tilts an object to be observed, for tilting said object to be observed in an angle step, and storing the obtained tiled image; a means for aligning the position of said tilted images; a means for generating an initial reconstructed image based on said tilted images; a means for projecting said initial reconstructed image at arbitrarily-defined angles and generating a plurality of projected images; a means for calculating errors in the corresponding pixels between the tilted images and the projection images; a means for determining a processing priority from said errors; a means for calculating the density for each gradation level; a means for determining the processing priority from said den sities; and a means for changing the density value of each pixel in the initial reconstructed image in each of the above-mentioned priorities.

22 Claims, 9 Drawing Sheets

(56) References Cited

FOREIGN PATENT DOCUMENTS

JP    2008-283892 A    11/2008
JP    2009-237704 A    10/2009

OTHER PUBLICATIONS

Jose-Maria Carazo et al., "Algorithms for 3D reconstruction", Joachim Frank, Electron Tomography 2 (2005), Springer, New York, pp. 228-231 (two (2) sheets).

Jose-Maria Carazo et al., "Algorithms for 3D reconstruction", Joachim Frank, Electron Tomography 2 (2005), Springer, New York, pp. 231-234 (three (3) sheets).

N. Baba et al., "A novel Method of Reconstructing a Tomogram by Convergence of an Innumerable Dots Map Without the 'Missing-Wedge' Effect", Frontiers of Electron Microscopy in Materials, S-15, Session-1, Oct. 2, 2009, p. 71 (one (1) sheet).

K.J. Batenburg et al., "3D imaging of nanomaterials by discrete tomography", Ultramicroscopy 109 (2009) pp. 730-740 (eleven (11) sheets).

\* cited by examiner

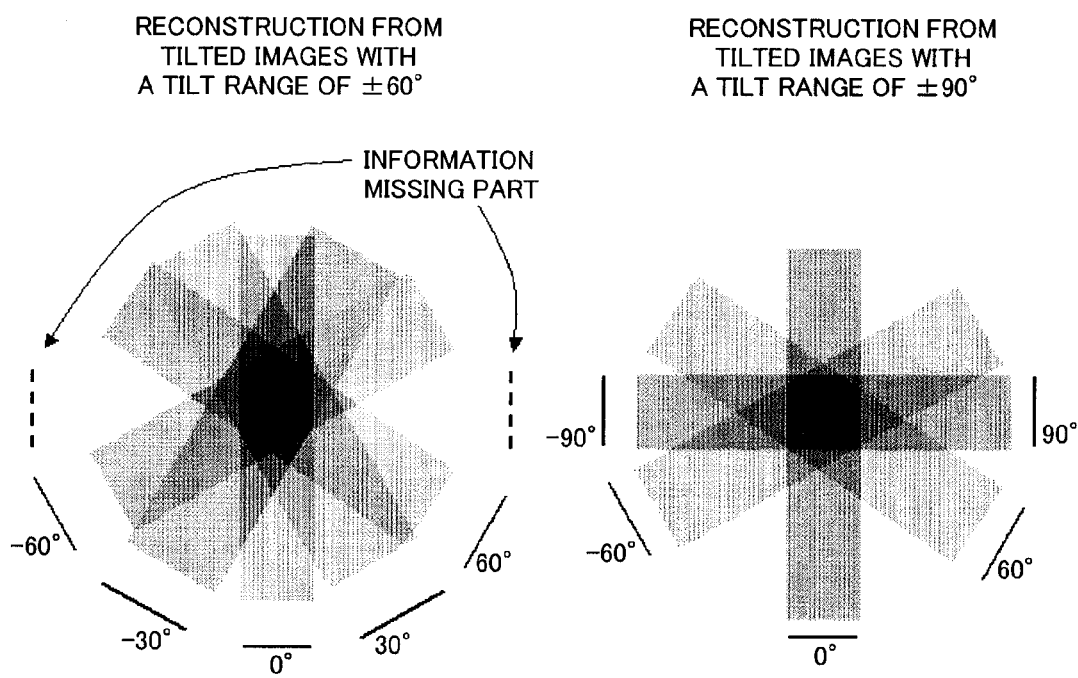
FIG. 1A
RECONSTRUCTION FROM TILTED IMAGES WITH A TILT RANGE OF ±60°
FIG. 1B
RECONSTRUCTION FROM TILTED IMAGES WITH A TILT RANGE OF ±90°
FIG. 1C
SHAPE OF STRUCTURE CONCEPT OF AN IMAGE IN THE PRIOR ART
(THE NUMERIC VALUES ARE GRAY LEVELS OF PIXELS)

CONCEPT OF AN IMAGE IN THE PRESENT INVENTION
(A GRAY LEVEL OF A PIXEL IS
A INTEGRATED VALUE OF QUANTUM UNITS)

UNKNOWN STRUCTURE (IMAGE)

NUMBER OF QUANTUM UNITS
FOR EACH PIXEL

INITIAL RECONSTRUCTED IMAGE

NUMBER OF QUANTUM UNITS
FOR EACH PIXEL

MODEL

RESULT OF THE PRESENT INVENTION

RESULT OF THE PRIOR ART

IMAGE PROCESSING METHOD, IMAGE PROCESSING SYSTEM, AND X-RAY COMPUTED TOMOGRAPHY SYSTEM

TECHNICAL FIELD

The present invention relates to image processing of objects to be observed by using electron beams or X-rays and, in particular, to a method for reconstructing a three-dimensional structure from two-dimensional images obtained.

BACKGROUND ART

There is increasing need to observe an object more intuitively in an electron microscope by reconstructing a three-dimensional structure from two-dimensional images obtained and, moreover, to extract and quantify any point in a reconstructed image. Various methods have been proposed to carry out such an observation.

For example, Non-Patent Document 1 discloses a back projection method of obtaining continuous tilted two-dimensional images by continuously tilting an object to be observed and reconstructing a three-dimensional image by doing back-projecting for each of the obtained continuous tilted two-dimensional images from the tilt angle at the time of obtainment, and Non-Patent Document 2 discloses a method of regarding the above-mentioned continuous tilted two-dimensional images as true value images in respective projection directions and then algebraically reconstructing an unknown three-dimensional image such that the errors between the results obtained by projecting the three-dimensional image in respective directions and the true values are minimum.

Additionally, Non-Patent Document 3 describes a dots concentration reconstruction technique, which is based on a concept that an image is a collection of dots, for optimizing the positions of dots in a three-dimensional image on the basis of the above-described continuous tilted two-dimensional images; and Non-Patent Document 4 describes a discrete algebraic reconstruction technique (DART) for creating a reconstructed image as a reference image using an algebraic reconstruction technique, dividing the reconstructed image into sections at a certain threshold value, and then reconstructing the image algebraically again using the information on the sections.

CITATION LIST

Non Patent Documents

Non Patent Document 1: Jose-Maria Carazo et al., Algorithms for 3D reconstruction, Joachim Frank, ELECTRON TOMOGRAPHY 2 (2005), Springer, New York, pp. 228-231

Non Patent Document 2: Jose-Maria Carazo et al., Algorithms for 3D reconstruction, Joachim Frank, ELECTRON TOMOGRAPHY 2 (2005), Springer, New York, pp. 231-234

Non Patent Document 3: N. Baba et al., Anovel Method of Reconstructing a Tomogram by Convergence of an Innumerable Dots Map Without the "Missing-Wedge" Effect, Frontiers of Electron Microscopy in Materials, S-15, Session-1, 2 Oct., 2009

Non Patent Document 4: K. J. Batenburg et al., 3D imaging of nanomaterials by disctrete tomography, Ultramicroscopy 1 09 (2009) 730-740

SUMMARY OF INVENTION

Technical Problem

In the techniques of Non Patent Documents 1 and 2, information on the reconstructed three-dimensional image does not contain information other than the tilt angles at the time of obtainment of the above-described continuous tilted two-dimensional images. Therefore, in order to carry out three-dimensional reconstruction with higher precision using the back projection technique or the algebraic reconstruction technique, the range of tilt angles needs to be set between −90° and +90°, and the increment in tilt angle needs to be set to be as small as possible, at the time of image obtainment.

Currently, however, an electron microscope used for general purposes is configured such that an object, processed into the form of a thin film, is placed on the sample holder to be observed. In observing an object under an electron microscope, there is a limit to tilting, or even when an object to be observed can be tilted sufficiently, there is a limit to the tilt angles because images cannot be formed due to a sample holder structure blocking the electron beams, for example. More specifically, when using an electron microscope used for general purposes, information missing parts occurs in the reconstructed three-dimensional image.

FIG. 1 shows reconstruction of a two-dimensional structure as an example. Reconstructing the two-dimensional structure requires a plurality of one-dimensional images obtained by tilting the structure and projecting it from different angles. FIG. 1 (a) shows reconstruction using one-dimensional images with a tilt range of ±60°. In this case, information from tilted images outside the range of ±60° are missing, resulting in more false images and missing parts of images than in the reconstructed image obtained by using one-dimensional images with a tilt range of ±90°, shown in FIG. 1B Moreover, the false images blurs the reconstructed structure, which makes it difficult to determine the boundary of the structure, resulting in poor quantitative performance. FIG. 1C shows the shape of the structure.

In addition, the above-described technique of Non-Patent Document 3 is a technique for complementing the information missing parts described above and is capable of significantly reducing false images and missing parts in reconstructed images. However, for this technique to be applied, the object to be observed requires being a single structural component. Structures which satisfy such a condition of application are limited, and therefore the technique is not versatile.

The above-described technique of Non-Patent Document 4 is a technique for filling in the information missing described above and is capable of significantly reducing false images and missing parts in reconstructed images. However, for this technique to be applied, the object to be observed requires being a known number of structural compositions. Since cases are limited where the number of the structural compositions of the structure to be reconstructed is known (in particular, the number of the structural compositions of a biotic structure is often unknown), samples to which this technique is applicable are limited.

The present invention was made in view of the various problems mentioned above, and therefore, it is an object of the present invention to provide image processing that significantly reduces false images and missing parts in reconstructed images, improves reconstruction accuracy and is applicable to observed objects that are composed of a plurality of components and applicable to samples having an unknown number of structural compositions.

Solution to Problem

According to one feature of the present invention for attaining the above-mentioned object, a method for processing images using an observation device including: an irradiation device for irradiating an object to be observed with electron beams or X-rays; a detector for detecting responses of the object occurring as a result of irradiation thereof; a holder unit for holding the object; a tilting device capable of arbitrarily setting a tilt angle of the object, comprising the following steps of:

tilting the object at predetermined angle steps;

storing the images which are obtained as 1st to Nth image data observed at respective tilt angles;

performing alignment calculation to align the stored 1st to Nth image data;

generating an initial reconstructed image from a projection image of the object;

projecting the reconstructed image at predetermined angles to generate and store 1st' to Nth' image data;

performing error calculation to calculate errors in corresponding pixels between the 1st to Nth images and the 1st' to Nth' images;

determining a processing priority order on the basis of the errors;

performing density calculation to calculate a density of pixels for each gradation level;

determining a processing priority order on the basis of the densities; and changing a gray level of each pixel in the reconstructed image in each of the processing priority orders.

The present invention has other various features for attaining the above-mentioned object, the details of which will be hereinafter described in the following embodiment.

Advantageous Effects of Invention

According to the present invention, it is possible to perform three-dimensional reconstruction complementing missing parts in images for even on objected objects composed of a plurality of components, and possible to significantly reduce false images and missing parts in a reconstructed image, resulting in a highly-precise three-dimensional reconstructed image.

BRIEF DESCRIPTION OF DRAWINGS

FIG. 1 shows false images and missing parts in a reconstructed image due to information missing, with FIG. A showing reconstruction from one-dimensional images with a tilt range of ±60°, FIG. B showing reconstruction from one-dimensional images with a tilt range of ±90°, and FIG. C showing the shape of the structure.

DESCRIPTION OF EMBODIMENTS

A preferred embodiment of the present invention will be described hereinafter with reference to the accompanying drawings. Examples described hereinafter are although explained using the embodiment of an electron microscope and its image processing, of course, the present invention is not to be limited thereto.

Also, one of features of the present invention is to reduce false images and missing parts which occur in a reconstructed image due to angular limitations on tilting by optimizing a gray level of each pixel of the reconstructed three-dimensional image. In the embodiment below, described is although reconstruction of a two-dimensional image, reconstruction of the two-dimensional image and reconstruction of a three-dimensional image are identical in principle since the three-dimensional image is a combination of a plurality of two-dimensional images in the thickness direction.

Figure 2:
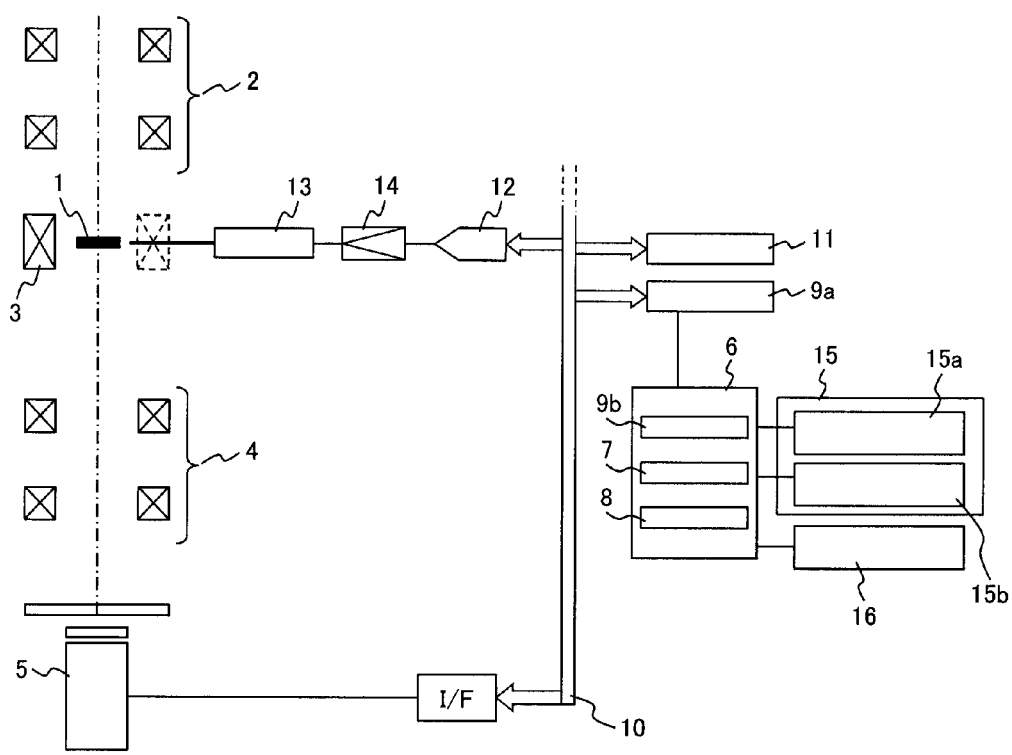
FIG. 2 is a schematic view of a system configuration in accordance with an embodiment of the present invention.

FIG. 2 shows an example of a system configuration in accordance with the present invention. The electron microscope of the present embodiment is provided with: an irradiation lens system 2 for irradiating a sample 1 with electron beams; an objective lens system 3 for bringing the sample into focus; a magnifying lens system 4 for magnifying an electron beam image which has passed through the sample; an image detector 5 for detecting the magnified image; a computer 6 for performing various kinds of calculation control processing; an arithmetic unit 7 in the computer; a storage unit 8 for storing data; communication interfaces 9a and 9b for carrying out communications between the computer and a microprocessor; the microprocessor 11 for sending control signals via a bus 10; a DAC 12 for digital-to-analog converting the signals outputted from the microprocessor 11; a power supply 14 for amplifying the signals outputted from the DAC 12 and outputting them to a sample tilting device 13; an input device 15 made up of a keyboard 15a and a mouse 15b for inputting parameters; and an output device 16 for outputting images.

A range of tilt angles and chopped tilt angles set at the input device 15 are sent from the communication interfaces 9a and 9b to the microprocessor 11 via the bus 10. Subsequently, they are inputted to the DAC 12 from the microprocessor 11 via the bus 10, amplified at the power supply 14, and outputted to the sample tilting device 13.

The sample 1 is continuously tilted by the sample tilting device 13 at chopped tilt angles within the range of tilt angles, and an image of the sample for each tilt angle is detected with the image detector 5. The images for respective tilt angles detected with the image detector 5 are stored as 1st to Nth images in the storage unit 8 in the computer. An initial reconstructed image is generated at the arithmetic unit 7 by using an image of a tilt angle near 0° from these stored images.

The initial reconstructed image is projected at the respective chopped tilt angles within the range of tilt angles to generate the 1st' to Nth' images, and respective errors between the 1st to Nth images and the 1st' to Nth' images are calculated by the arithmetic unit 7. The gray level of the initial reconstructed image is optimized with the arithmetic unit 7 such that the errors become a minimum, and the optimized image is stored in the storage unit 8.

Subsequently, at the arithmetic unit 7, the gray level of the initial reconstructed image are optimized under a constraint that any structure is needed to form a continuum and stored in the storage unit 8. By repeating the calculation described above until the conditions of these different optimization methods are satisfied, a three-dimensional image with less false images and missing parts which occur due to angular limitations on tilting can be reconstructed.

Processing performed by the arithmetic unit 7 in accordance with the present invention will be hereinafter explained in detail by using reconstruction of a two-dimensional image as an example. However, the present embodiment is not to be construed as limiting the scope of the present invention.

Figure 3A:
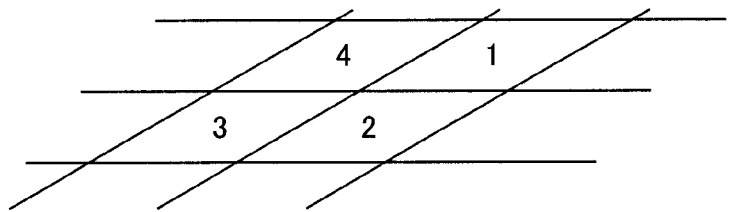
FIG. 3 shows the concept of image gray levels in accordance with the present embodiment, with FIG. 3A showing the concept of an image in the prior art (the numeric values are the gray levels of the pixels) and FIG. 3B showing the concept of an image in the present invention (the gray level of a pixel is the integrated value of quantum units).
Figure 3B:
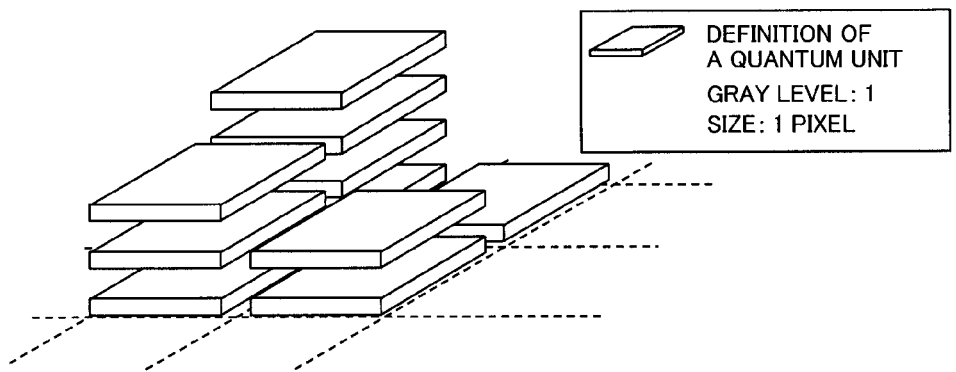

First, described is the concept of an image in the present embodiment. An image is defined as an arrangement of pixels having various gray levels. In other words, a two-dimensional image is a two-dimensional arrangement of gray levels. As shown in FIG. 3, however, in the present embodiment, a gray level is quantized and defined as a quantum unit, and the gray level of a pixel is expressed in the integrated value of quantum units. More specifically, a two-dimensional image is a three-dimensional arrangement of quantum units.

Now, described is reconstruction in the present embodiment. As shown by the prior art mentioned above, an unknown two-dimensional image can be reconstructed by using a plurality of one-dimensional images obtained by projecting the two dimensional image from various directions. Similarly, an unknown three-dimensional image can be reconstructed from a plurality of two-dimensional projection images. As is the case with the prior art, also in the present embodiment, the reconstruction is carried out using a plurality of projection images. Projection images obtained by projecting an object to be reconstructed in various directions are defined as the 1st to Nth images, and the projection directions are defined as the 1st to Nth directions.

A one-dimensional projection image results from compression of a two-dimensional image in the projection direction, and a total value of gray levels of the reconstructed image can be determined on the basis of one projection image. Also, the total number of quantum units in the reconstructed image can be determined on the basis of the total value of the gray levels. In other words, a two-dimensional image can be reconstructed by rearranging all the quantum units to their correct positions using a one-dimensional projection image.

Next, a method for rearranging quantum units to their correct positions in a reconstructed image will be described.

A projection image contains information on the amount of quantum units and information on their positions in a direction perpendicular to the projection direction. However, the Projection image does not contain information as to positions in the projection direction. Information as to the positions in the projection direction can be derived from images projected in various directions.

Figure 4:
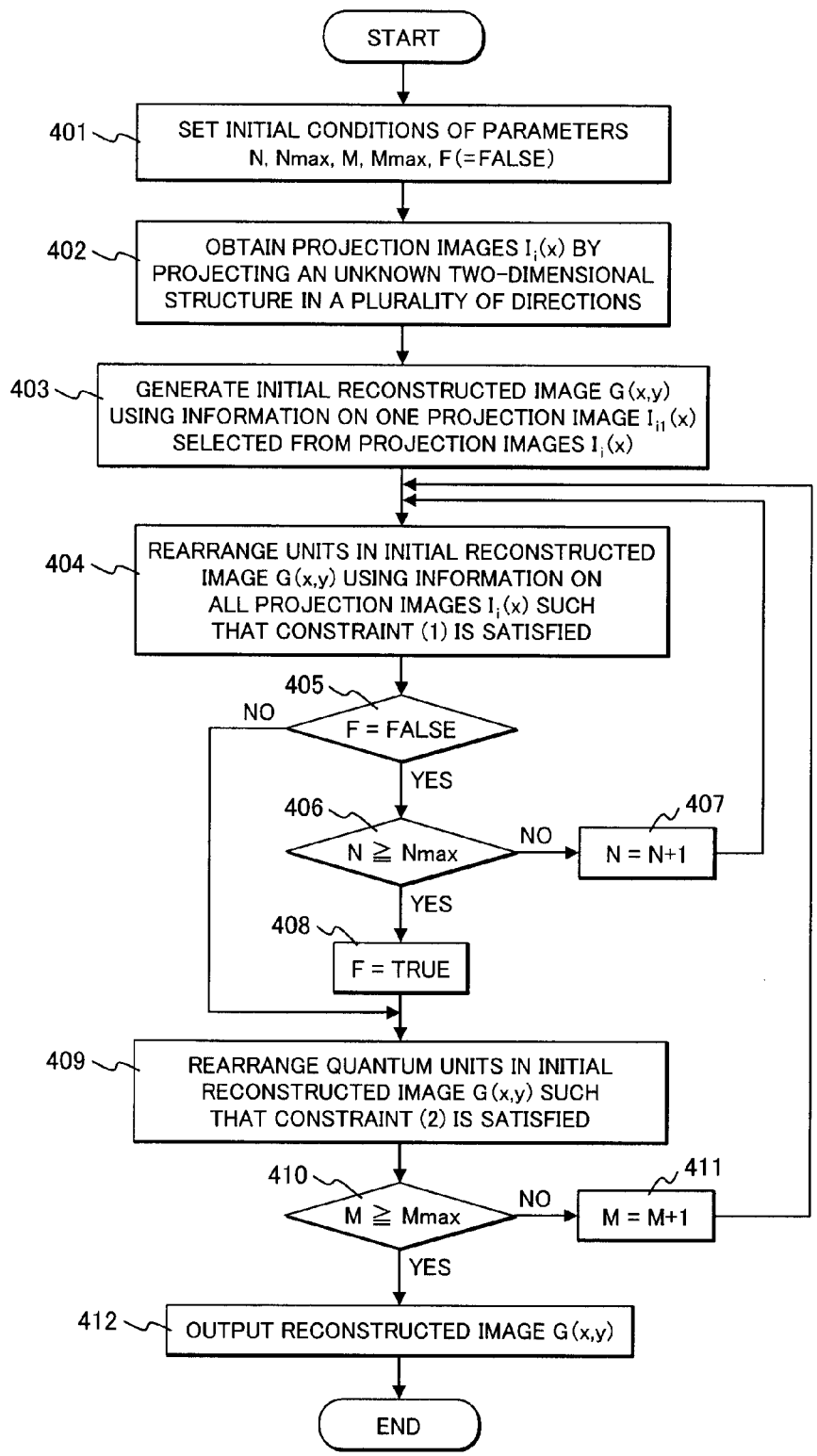
FIG. 4 is a schematic flow diagram showing a processor for rearranging quantum units in accordance with the present embodiment.

FIG. 4 shows a schematic flow of a quantum unit rearrangement unit in accordance with the present embodiment. First of all, initial conditions of parameters are set. Herein, N and M represent counters, Nmax and Mmax represent the numbers of iterations, and F represents a flag for judging the necessity of repeating step 404.

Next, at step 402, projection images $I_i$ (x) obtained by projecting an unknown two-dimensional structure in a plurality of directions are inputted. And then at step 403, an initial reconstructed image G (x,y) is generated using information on one projection image $I_i$ (x) selected from the images $I_i$ (x).

Next, all the quantum units of the reconstructed image G (x,y) are rearranged using images obtained by projecting the reconstructed image G (x,y) and the information on all the projection images $I_i$ (x) inputted at step 402 (step 404). This step will be described in detail below referring to FIG. 6 and FIG. 7.

Subsequently, a flag judgment is made at step 405, and when the flag is "false," the current loop count is determined at step 406. When the loop count is less than a specified count, step 404 is repeated until it reaches the specified count. After the system exits from the loop, the flag is changed to "true" and the process of step 409 is carried out.

At step 409, a constraint that any structure is needed to form a continuum is placed on the reconstructed image G (x,y), and the quantum units in the reconstructed image G (x,y) are rearranged such that this constraint is satisfied. This step will be described in detail below with reference to FIG. 8 and FIG. 9.

Subsequently, the loop count is determined at step 410, and when the loop count is less than a specified count, the system goes back to step 404. At this point, since the flag is "true," the system does not loop step 404 and goes to step 409. When the judgment condition of step 410 is satisfied, the reconstructed image is outputted at step 412 to complete reconstruction.

Each step will be hereinafter described in detail one by one.

Figure 5A:
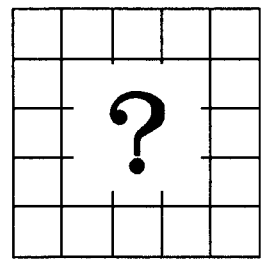
FIG. 5 illustrates a method for generating an initial reconstructed image in the present embodiment, with FIG. A showing an unknown structure (image), FIG. B showing the relationship between a pixel one-dimensional image and the number of quantum units for each pixel, and FIG. C showing the relationship between an initial reconstructed image and the number of quantum units for each pixel.
Figure 5B:
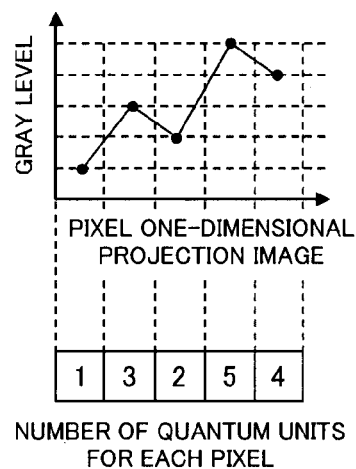
Figure 5C:
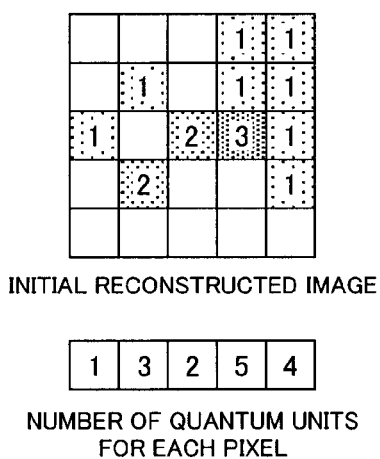

At step 403, generated is a two-dimensional image where each side thereof is the same as the corresponding side of the projection image and the gray level of each pixel is 0. Next, as shown in FIGS. 5A-5C, the amount of quantum units and their positions in the direction perpendicular to the projection direction are determined on the basis of a one-dimensional projection image of FIG. 5B which is obtained by projecting an unknown structure of FIG. 5A. Therefore, the quantum units are rearranged in the two-dimensional image such that this condition is satisfied to generate an initial reconstructed image of FIG. 5C. The positional information in the projection direction is determined using random numbers. The quantum units arranged in the initial reconstructed image are controlled individually, and the gray levels of all the pixels in the reconstructed image are optimized by moving each quantum unit.

Figure 6:
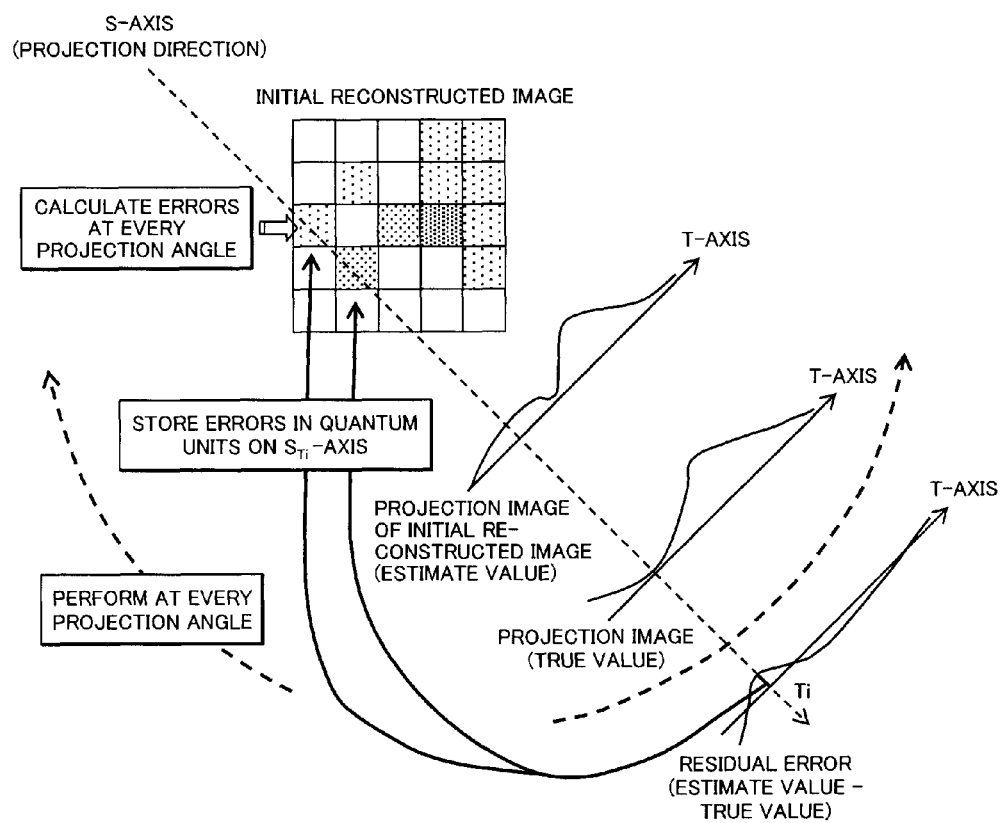
FIG. 6 illustrates a method for calculating the integrated value of residual errors for each quantum unit in the present embodiment.

At step 404, first of all, the initial reconstructed image is projected in the 1st to Nth directions to generate the 1st' to Nth' projection images. As shown in FIG. 6, the 1st to Nth projection images and the 1st' to Nth' projection images are defined as true values and estimate values, respectively, and each residual error between projection images in the same direction is calculated. The axis in each projection direction is defined as the S-axis, and the axis perpendicular to the S-axis is defined as the T-axis. The value of the error at a coordinate $T_i$ is stored in all the quantum units existing on the S-axis which passes through the coordinate $T_i$ ($S_{Ti}$-axis). This is done for every projection direction, and the integrated value of all the residual errors associated with each quantum unit is stored in the quantum unit. Subsequently, the quantum units to be moved are rearranged in descending order of the integrated values for all the quantum units and prioritized.

Next, the destination of each quantum unit is determined. The destination determination process is performed on the quantum units in descending order of the priority. This destination determination is largely divided into two sub-processes. In the first sub-process, the temporary destination of each quantum unit in each projection direction is determined, and then in the second sub-process, the actual destination thereof is determined on the basis of the average value of amounts of movements for temporary destinations.

Figure 7:
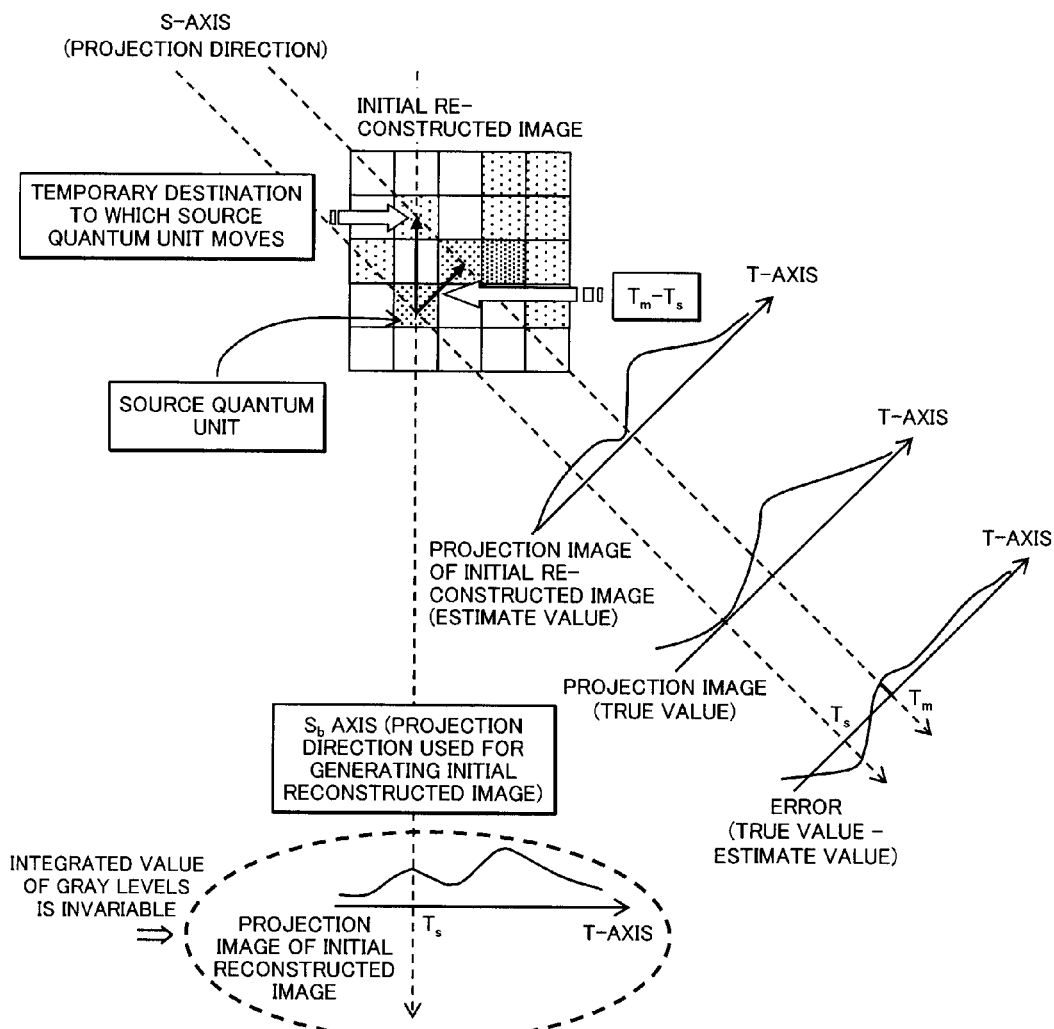
FIG. 7 illustrates a method for deriving interim destinations in the present embodiment.

In the first sub-process, as illustrated in detail in FIG. 7, errors between the 1st projection image (true value) and the 1st' projection image (estimate value) are calculated, and a coordinate Tm having the largest error is calculated. The temporary destination in the 1st projection direction of the quantum unit on which the destination determination process is being performed is the position where the error of the coordinate Tm is reduced. At this point, the following constraint is placed on the movement of the quantum unit to be moved.

<Constraint (1)>

All the projection images to be used for CT are to be obtained by projecting an unknown tomogram, and since the gray levels of each projection image are inevitably determined by the projection direction, the integrated value of gray levels in the projection direction used for generating the initial reconstructed image has always to be the same in the initial reconstructed image. Therefore, the direction of movement of each quantum unit is limited to the projection direction in which the initial reconstruction image is generated.

Under above constraint, when a coordinate on the T-axis of a source quantum unit is Ts, a coordinate of intersection between a line $S_{Tm}$ which passes through the coordinate Tm on the T-axis in the 1st projection direction (S-axis) and a line $S_{bTs}$ which passes through the coordinate Ts on the T-axis in the projection direction ($S_b$-axis) in which the initial reconstructed image is generated, is defined as the temporary destination to which the source quantum unit moves.

Subsequently, a temporary destination of a quantum unit having a second priority after the quantum unit whose destination has been determined as above is determined in the same manner. At this point, a coordinate Tm' having the maximum error is calculated using the result obtained by subtracting a gray level for one quantum unit from the value of the coordinate Tm having the largest error. The above process is performed on every quantum unit in descending order of the priority, and the temporary destination in the 1st projection direction of every quantum unit is determined. Also, the temporary destination of every quantum unit in the 2nd to Nth projection directions is determined in the same manner as the one described above.

As described above, the temporary destination for every quantum unit in every projection direction is determined in the first sub-process, and the actual destination of every quantum unit is determined in the second sub-process. In the present embodiment, the actual destination is defined as the average value of amounts of movements to temporary destinations in all the projection directions.

In the above-described process, every quantum unit is moved to its destination, and the judgment of step 406 is made. Subsequently, the process at step 404 is repeated until the judgment condition is satisfied. While the actual destination of each quantum unit is defined as the average value of amounts of movements to temporary destinations in all the projection directions, the algorithm which determines the actual destination may use a median or a mode instead of the average value.

In step 409, the quantum units are rearranged in a manner different from that of step 404. In this process, no projection images are used, and rearrangement is carried out on the basis of the information on the initial reconstructed image only.

Figure 8:
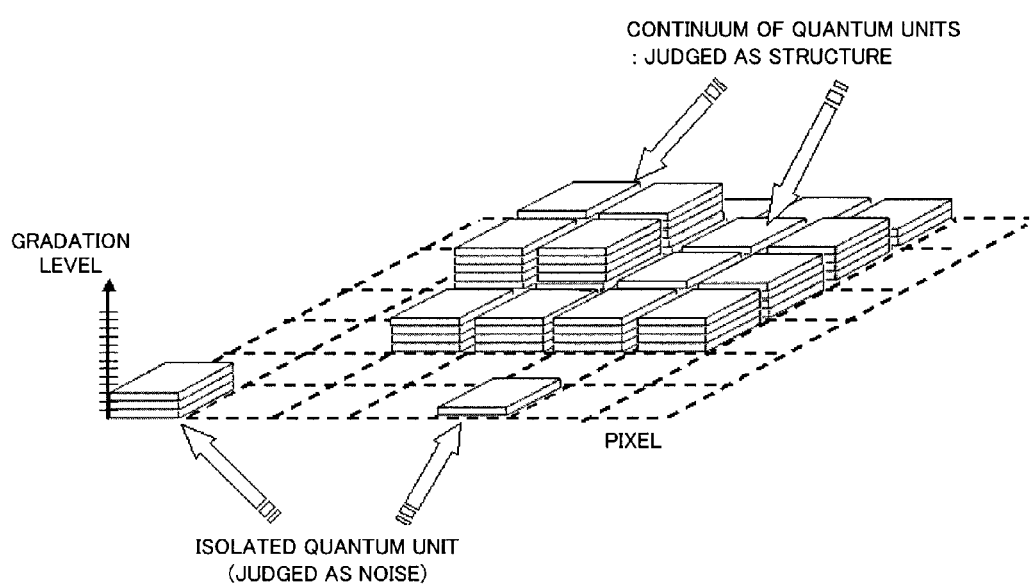
FIG. 8 is a conceptual diagram of a structure in an image in the present embodiment.

As shown in FIG. 8, in general, in order to recognize a structure in an image, more than a few pixels of the same gradation level need to exist successively. On the basis of the concept above, in the process at step 409 the following constraint is placed on the initial reconstructed image, and rearrangement is carried out such that this constraint is satisfied.

<Constraint (2)>

While pixels for the respective gradation levels may be dispersed from each other, these pixels need to be form a continuous pixel group to be recognized as the structure.

In the present embodiment, since the gray levels of an image are expressed in the integrated value of quantum units, when the gray level of a quantum unit is defined as a unit gradation level, the initial reconstructed image can be divided according to gradation level. In other words, an image which satisfies the above constraint can be reconstructed by moving the quantum units such that the quantum units existing at each gradation level form a continuous pixel group to each other. Processing with respect to moving the quantum units using the above constraint will be described in detail below.

First of all, the quantum units which are to be moved to satisfy the above constraint are selected from all the quantum units in the initial reconstructed image. In the present embodiment, the density of the quantum units which exist within a pixel section around a quantum unit of interest is used to judge whether the section is a continuum or not. In other words, a threshold is provided for the density, and the section is regarded as a continuum when the density is equal to or over the threshold. So, the quantum units to be moved are selected by calculating the above density for every quantum unit and regarding every quantum unit having a density less than the threshold as a quantum unit to be moved.

Figure 9:
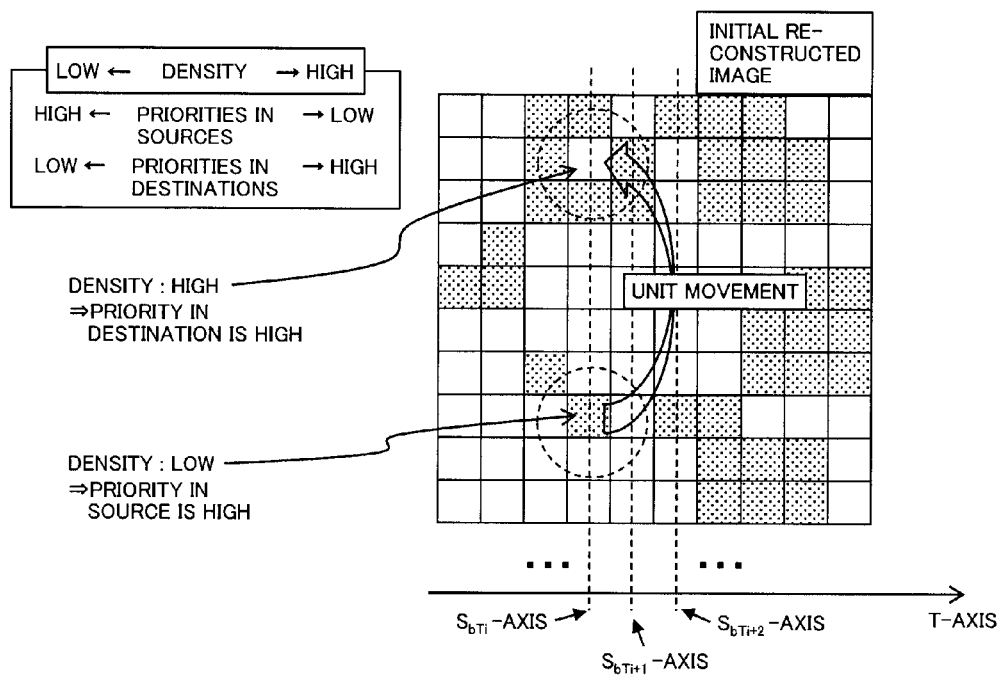
FIG. 9 illustrates a quantum unit rearrangement process with continuum formation as a constraint in the present embodiment.

Next, the quantum units to be moved are determined to be assigned priorities for movement. These priorities are not determined within the image where the quantum units to be moved exist, but it is determined within axes where the quantum units exist, as shown in FIG. 9. In the present embodiment, the axes ($S_b$-axes) are parallel to the projection direction used for generating the initial reconstructed image, and each of them is an axis which passes through a coordinate on the T-axis, which is perpendicular to the $S_b$-axes (for example, when each axis passes through a coordinate Ti, it is the $S_{bTi}$-axis, and when it passes through a coordinate $T_{i+1}$, it is the $S_{bTi+1}$-axis). Also, the lower the density of the quantum unit is, the higher priority is given.

Density calculation in the present embodiment is carried out by providing a section around a quantum unit to be given a certain degree of priority and determining the ratio between the number of pixels within the section and the number of quantum units of the same gradation level as the quantum unit within the section (the number of quantum units/the number of pixels). This calculation is performed on every quantum unit which exists within the $S_b$-axis, and the quantum units are prioritized for movement in the order of lowest to highest in terms of the above ratio.

Subsequently, destinations for quantum unit are prioritized. As is the case with the prioritization described above, this prioritization is performed also on the basis of the ratio between the number of pixels and the number of quantum units within a section. In this process, the density calculation is performed on every pixel on the $S_b$-axis, and the pixels are prioritized in becoming a destination in the order of highest to lowest in terms of the above ratio.

The quantum units having a higher priority in source moved are moved to the pixels having a higher priority in becoming a destination, and quantum unit rearrangement with Ti as the coordinate on the T-axis is completed. Subsequently, this rearrangement process is carried out as the coordinate on the T-axis is shifted to Ti+1, Ti+2, . . . in succession.

When the rearrangement on all axes is completed, the quantum unit rearrangement in this process is completed.

After the rearrangement process at step 409, when the judgment condition of step 410 is satisfied, the initial reconstructed image is outputted, thereby completing the reconstruction processing. When the judgment condition of step 410 is not satisfied, the system goes back to step 404, and the rearrangement processing at step 404 and step 409 is repeated until the judgment condition is satisfied.

Figure 10A:
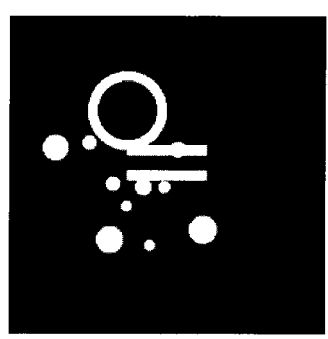
FIG. 10 shows comparison of results of reconstruction using a model between the present embodiment and the prior art, with FIG. 10A showing the model, FIG. 10B showing the result of the present embodiment, and FIG. 10C showing the result of the prior art.
Figure 10B:
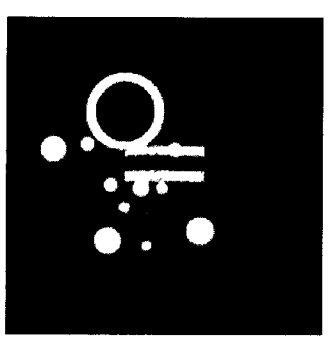
Figure 10C:
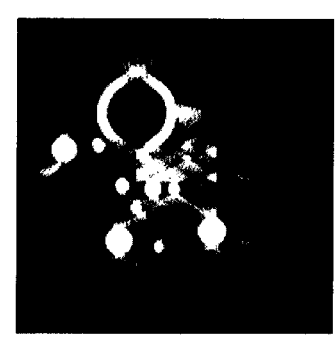

FIG. 10 shows exemplary comparison of results of reconstruction using a model between the present embodiment and the prior art. FIG. 10A shows the model, FIG. 10B shows the result of the present embodiment, and FIG. 10C shows the result of the prior art. In the model, the object to be observed has a tilt angle range from −60° to +60° with a chopped tilt angle of 2°.

In the result of the prior art, there are many false images around each structure. Also, the image of the ring-shaped portion is partially missing and does not form a continuum, and the images of the bar-shaped portions are missing in the middle and do not form continuums. In contrast, in the result of the present embodiment, there are significantly less such false images and missing parts.

Lastly, in the description above, judgment is although made on the basis of the number of iterations at step 406 and 410, the method of judgment at these steps is not limited to this and judgment may be made on the basis of errors with projection images, etc.

While electron beam computed tomography using an electron microscope is used as an example in the above embodiment, the present invention is applicable to X-ray computed tomography as well. In this case, the irradiated radiation is X-rays instead of electron beams. However, all else is the same as in the case with electron beam computed tomography.

The present invention can provide with widespread application in the field of material analysis, allowing visualization and measurement of three-dimensional shapes of semiconductor devices, particle size measurement and distribution observation of catalyst particles, and accurate three-dimensional material analysis of nano materials. Also, possible applications of the present invention for cells and high-polymer materials include visualization of the geometries of organelles and observation of component mixtures.

Moreover, when applied to electron beam computed tomography, X-ray computed tomography, etc., the present invention is expected to reduce sample damage and the level of exposure.

In the embodiment described above, each component of any structure to be observed is subject to a constraint that it form a continuum, and continuum formation is judged on the basis of the density of pixels (the density of quantum units) having a gray level identical to or greater than a predetermined gray level. In addition to that, the threshold value of the density for judgment may be set at any value.

In the embodiment above, the arithmetic unit 7 performs of: calculating errors in the corresponding pixels between the 1st to Nth images, which are true values, and the 1st' to Nth' images, which are estimate values; determining a processing priority order on the basis of the errors; calculating a density of pixels for each gradation level; determining a processing priority order on the basis of the densities; and changing the gray level of each pixel in the reconstructed image in each of the processing priority orders. Further, a pixel section resulting from such a method for processing images may be defined for each gray level or any range of gray levels.

Furthermore, by using the image processing result concerning the definition of the section described above, and by using information obtained from an observation device, the volume and/or the surface area of any section, and the number and/or the mass of continuous sections etc. of the object to be observed may be calculated.

Also, the number of iterations of the error calculation and the number of iterations of the density calculation may be set individually.

In addition, as an image processing storage medium for performing the image processing in the embodiment described above, the following is suggested.

An image processing storage medium in an observation device including: a detector for irradiating an object to be observed with electron beams or X-rays and detecting responses of the object occurring as a result of irradiation thereof; a holder unit for holding the object; a tilting device capable of arbitrarily setting a tilt angle of the object, an image storage medium for storing images which are obtained as 1st to Nth image data observed at respective tilt angles by tilting the object at predetermined angle steps; and a calculation part for performing alignment calculation to align the stored 1st to Nth image data; wherein the image processing storage medium is configured to store a program comprising the following steps of: generating an initial reconstructed image from a projection image of the object; projecting the reconstructed image at predetermined angles to generate and store 1st' to Nth' image data; performing error calculation to calculate errors in corresponding pixels between the 1st to Nth images and the 1st' to Nth' images; determining a processing priority order on the basis of the errors; performing density calculation to calculate a density of pixels for each gradation level; determining a processing priority order on the basis of the densities; and changing a gray level of each pixel in the reconstructed image in each of the processing priority orders.

(i) In the storage medium described above, each of the gray levels of the image may be the integrated value of unit gray levels.

(ii) In the storage medium described above, a total value of the unit gray levels may be the same in all the projection images.

(iii) In the storage medium described above, a constraint may be placed on the initial reconstructed image such that the total value of unit gray levels in a direction parallel to a projection direction for generating the image is invariable.

(iv) In the storage medium described above, a constraint may be placed such that each component of any structure in the initial reconstructed image forms a continuum.

(v) In the storage medium described above, whether any structure in the initial reconstructed image forms a continuum or not may be judged on the basis of the density of pixels having a gray level identical to or greater than a predetermined gray level.

(vi) In the storage medium described above, in the density judgment processing described above, a threshold value of the density for judgment may be set at any value.

(vii) In the storage medium described above, the number of iterations of the error calculation and the number of iterations of the density calculation may be set individually.

Additionally, the following image processing storage medium is also proposed.

An image processing storage medium in an observation device including: a detector for irradiating an object to be observed with electron beams or X-rays and detecting responses of the object occurring as a result of irradiation thereof; a holder unit for holding the object; a moving device capable of arbitrarily setting a position of the irradiation device around the object; an image storage medium for storing images which are obtained as 1st to Nth image data observed for respective movement angles by moving the object at predetermined angle steps; and a calculation part for performing alignment calculation to align the stored 1st to Nth image data; wherein the image processing storage medium is configured to store a program comprising the following steps of: generating an initial reconstructed image from a projection image of the object;

projecting the reconstructed image at predetermined angles to generate and store 1st' to Nth' image data;

performing error calculation to calculate errors in corresponding pixels between the 1st to Nth images and the 1st' to Nth' images;

determining a processing priority order on the basis of the errors;

performing density calculation to calculate a density of pixels for each gradation level;

determining a processing priority order on the basis of the densities; and changing a gray level of each pixel in the reconstructed image in each of the processing priority orders.

This image processing storage medium may also have the features (i) to (vii) described above.

In the image processing system described in the embodiment above, a parallel image processing may be performed by setting the number of iterations of the error calculation and the number of iterations of the density calculation at different values from each other so that a plurality of results can be derived.

In addition, the parallel processing described above may be performed by using a plurality of personal computers.

REFERENCE SIGNS LIST

1: SAMPLE, 2: IRRADIATION LENS SYSTEM, 3: OBJECTIVE LENS SYSTEM, 4: MAGNIFYING LENS SYSTEM, 5: IMAGE DETECTOR, 6: COMPUTER, 7: INTERNAL ARITHMETIC UNIT: 8: STORAGE UNIT, 9a, 9b: COMMUNICATION INTERFACE, 10: BUS, 11: MICROPROCESSOR, 12: DAC (DIGITAL-TO-ANALOG CONVERTER), 13: SAMPLE TILTING DEVICE, 14: POWER SUPPLY, 15: INPUT DEVICE, 16: OUTPUT DEVICE

The invention claimed is:

1. A method for processing images using an observation device including: an irradiation device for irradiating an object to be observed with electron beams or X-rays; a detector for detecting responses of the object occurring as a result of irradiation thereof; a holder unit for holding the object; a tilting device capable of arbitrarily setting a tilt angle of the object, comprising the following steps of:

tilting the object at predetermined angle steps;

storing the images which are obtained as 1st to Nth image data observed at respective tilt angles;

performing alignment calculation to align the stored 1st to Nth image data;

generating an initial reconstructed image from a projection image of the object;

projecting the reconstructed image at predetermined angles to generate and store 1st' to Nth' image data;

performing error calculation to calculate errors in corresponding pixels between the 1st to Nth images and the 1st' to Nth' images;

determining a processing priority order on the basis of the errors;

performing density calculation to calculate a density of pixels for each gradation level;

determining a processing priority order on the basis of the densities; and changing a gray level of each pixel in the reconstructed image in each of the processing priority orders.

2. The method for processing images according to claim 1, wherein each of the gray levels of the image is an integrated value of unit gray levels.

3. The method for processing images according to claim 1, wherein a total value of the unit gray levels is the same in all the projection images.

4. The method for processing images according to claim 1, wherein a constraint is placed on the initial reconstructed image such that the total value of unit gray levels in a direction parallel to a projection direction for generating the image is invariable.

5. The method for processing images according to claim 1, wherein a constraint is placed such that each component of any structure forms a continuum.

6. The method for processing images according to claim 5, wherein whether the structure forms the continuum or not is judged on the basis of the density of pixels having a gray level identical to or greater than a predetermined gray level.

7. A method for processing images to define a section of a result obtained by the method for processing images according to claim 1 for each gray level or any range of gray levels.

8. A method for processing images using an observation device including: an irradiation device for irradiating an object to be observed with electron beams or X-rays; a detector for detecting responses of the object occurring as a result of irradiation thereof; a holder unit for holding the object; and a moving device capable of arbitrarily setting a position of the irradiation device around the object, comprising the following steps of:

moving the irradiation device at predetermined angle steps;

storing images which are obtained as 1st to Nth image data observed at respective movement angles;

performing alignment calculation to align the stored 1st to Nth image data;

generating an initial reconstructed image from a projection image of the object;

projecting the reconstructed image at predetermined angles to generate and store 1st' to Nth' image data;

performing error calculation to calculate errors in corresponding pixels between the 1st to Nth images and the 1st' to Nth' images;

determining a processing priority order on the basis of the errors;

performing density calculation to calculate a density of pixels for each gradation level;

determining a processing priority order on the basis of the densities; and changing a gray level of each pixel in the reconstructed image in each of the processing priority orders.

9. The method for processing images according to claim 8, wherein each of the gray levels of the image is an integrated value of unit gray levels.

10. The method for processing images according to claim 8, wherein a total value of the unit gray levels is the same in all the projection images.

11. The method for processing images according to claim 8, wherein a constraint is placed on the initial reconstructed image such that the total value of unit gray levels in a direction parallel to a projection direction for generating the image is invariable.

12. The method for processing images according to claim 8, wherein a constraint is placed such that each component of any structure forms a continuum.

13. The method for processing images according to claim 12, wherein whether the structure forms a continuum or not is judged on the basis of the density of pixels having a gray level identical to or greater than a predetermined gray level.

14. A method for processing images to define a section of a result obtained by the method for processing images according to claim 8 for each gray level or any range of gray levels.

15. An X-ray computed tomography system using an observation device including: an irradiation device for irradiating an object to be observed with electron beams or X-rays; a detector for detecting responses of the object occurring as a result of irradiation thereof; a holder unit for holding the object; and a moving device capable of arbitrarily setting a position of the irradiation device around the object, the system further comprising:
 a moving section configured to move the irradiation device at predetermined angle steps;
 a storage section configured to store images which are obtained as 1st to Nth image data observed at respective movement angles;
 a calculation section configured to perform alignment calculation to align the stored 1st to Nth image data;
 an image generating section configured to generate an initial reconstructed image from a projection image of the object;
 a projecting section configured to project the reconstructed image at predetermined angles to generate and store 1st' to Nth' image data;
 an error calculating section configured to perform error calculation to calculate errors in corresponding pixels between the 1st to Nth images and the 1st' to Nth' images;
 a determination section configured to determine a processing priority order on the basis of the errors;
 a calculation section configured to perform density calculation to calculate a density of pixels for each gradation level;
 a determination section configure to determine a processing priority order on the basis of the densities; and
 a gray level changing section configured to change the gray level of each pixel in the reconstructed image in each of the processing priority orders.

16. An image processing system using an observation device including: an irradiation device for irradiating an object to be observed with electron beams or X-rays; a detector for detecting responses of the object occurring as a result of irradiation thereof; a holder for holding the object; and a tilting device capable of arbitrarily setting a tilt angle of the object, the system further comprising:
 a tilting section configured to tilt the observation device at predetermined angle steps;
 a storage section configured to store the images which are obtained as 1st to Nth image data at respective tilt angles;
 a calculation section configured to perform alignment calculation to align the stored 1st to Nth image data;
 an image generating section configured to generate an initial reconstructed image from a projection image of the object;
 a projecting section configured to project the reconstructed image at predetermined angles to generate and store 1st' to Nth' image data;
 an error calculating section configured to perform error calculation to calculate errors in corresponding pixels between the 1st to Nth images and the 1st' to Nth' images;
 a determination section configured to determine a processing priority order on the basis of the errors;
 a calculation section configured to perform density calculation to calculate a density of pixels for each gradation level;
 a determination section configure to determine a processing priority order on the basis of the densities; and
 a gray level changing section configured to change the gray level of each pixel in the reconstructed image in each of the processing priority orders.

17. The image processing system according to claim 16, wherein the number of iterations of the error calculation and the number of iterations of the density calculation can be set individually.

18. An image processing system using an observation device including: an irradiation device for irradiating an object to be observed with electron beams or X-rays; a detector for detecting responses of the object occurring as a result of irradiation thereof; a holder unit for holding the object; and a moving device capable of arbitrarily setting a position of the irradiation device around the object, the system further comprising:
 a moving section configured to move the irradiation device at predetermined angle steps;
 a storage section configured to store images which are obtained as 1st to Nth image data observed at respective movement angles;
 a calculation section configured to perform alignment calculation to align the stored 1st to Nth image data;
 an image generating section configured to generate an initial reconstructed image from a projection image of the object;
 a projecting section configured to project the reconstructed image at predetermined angles to generate and store 1st' to Nth' image data;
 an error calculating section configured to perform error calculation to calculate errors in corresponding pixels between the 1st to Nth images and the 1st' to Nth' images;
 a determination section configured to determine a processing priority order on the basis of the errors;
 a calculation section configured to perform density calculation to calculate a density of pixels for each gradation level;
 a determination section configure to determine a processing priority order on the basis of the densities; and
 a gray level changing section configured to change the gray level of each pixel in the reconstructed image in each of the processing priority orders.

19. The image processing system according to claim 18, wherein the number of iterations of the error calculation and the number of iterations of the density calculation can be set individually.

20. The image processing system according to claim 18, further comprising:
    an image/gradation level changing section configured to change the image data to gradation-level representations;
    a gradation composition/image changing section configured to change each composition of the gradation-level representations to image data using a plurality of images; and
    a gradation/image changing section configured to change the gradation-level representations to image data.

21. The image processing system according to claim 20, wherein each composition of the gradation-level representations is changed using a plurality of images such that it forms a continuum.

22. The image processing system according to claim 21, wherein whether each composition of the gradation-level representations forms a continuum or not is judged on the basis of the density of each composition of the gradation-level representations.

* * * * *